United States Patent
Novak et al.

(10) Patent No.: US 7,429,257 B2
(45) Date of Patent: Sep. 30, 2008

(54) INSTRUMENT THAT CAN BE INSERTED INTO THE HUMAN BODY

(75) Inventors: Pavel Novak, Schaffhausen (CH); Jürgen Kraft-Kivikoski, Radolfzell (DE); Helmut Wehrstein, Tuttlingen (DE)

(73) Assignee: Storz Endoskop GmbH (CH)

( * ) Notice: Subject to any disclaimer, the term of this patent is extended or adjusted under 35 U.S.C. 154(b) by 768 days.

(21) Appl. No.: 10/761,975

(22) Filed: Jan. 21, 2004

(65) Prior Publication Data

US 2004/0153030 A1     Aug. 5, 2004

Related U.S. Application Data

(60) Division of application No. 08/946,799, filed on Oct. 8, 1997, now Pat. No. 6,814,714, which is a continuation of application No. 08/530,150, filed as application No. PCT/DE94/00663 on Jun. 15, 1994, now abandoned.

(30) Foreign Application Priority Data

Jun. 15, 1993   (DE)  .................................. 43 19 630

(51) Int. Cl.
     *A61B 18/14*   (2006.01)
(52) U.S. Cl. ..................................... 604/114
(58) Field of Classification Search ............. 604/93.01, 604/113, 114, 158, 264, 23–27, 31, 164.01, 604/247, 65, 67, 190, 131, 151; 606/27, 606/31, 32, 42; 607/98, 96, 102, 105, 107, 607/113; 165/175, 177, 178, 181, 184, 154; 261/104, 154, DIG. 65; 600/158, 156, 159
See application file for complete search history.

(56) References Cited

U.S. PATENT DOCUMENTS

| | | | |
|---|---|---|---|
| 1,369,010 A | 3/1921 | Pieper et al. | |
| 4,248,217 A | 2/1981 | Brisson | |
| 4,464,169 A * | 8/1984 | Semm | 604/26 |
| 4,682,010 A | 7/1987 | Drapeau et al. | 219/381 |
| 4,715,372 A * | 12/1987 | Philippbar et al. | 606/2 |
| 4,808,168 A * | 2/1989 | Warring | 604/158 |
| 4,869,717 A * | 9/1989 | Adair | 604/506 |
| 4,878,894 A * | 11/1989 | Sutter et al. | 604/24 |
| 4,966,578 A * | 10/1990 | Baier et al. | 604/26 |
| 5,139,478 A * | 8/1992 | Koninckx et al. | 604/26 |
| 5,199,604 A | 4/1993 | Palmer et al. | 222/25 |
| 5,362,310 A * | 11/1994 | Semm | 604/26 |
| 5,364,365 A * | 11/1994 | Wortrich | 604/158 |

(Continued)

*Primary Examiner*—Nicholas D. Lucchesi
*Assistant Examiner*—Christopher D Koharski
(74) *Attorney, Agent, or Firm*—St. Onge Steward Johnston & Reens LLC

(57) ABSTRACT

An endoscopic instrument includes a first instrument part adapted for introduction into a cavity of a human body and having an introduction channel therein for passage of gas therethrough, and a second instrument part having a connection channel therein adapted to be connected to the first instrument part introduction channel. The second instrument part is adapted for connection to a gas source to provide gas, at a flow rate suitable for insufflation of a human body cavity, from the gas source through the connection channel to the introduction channel for introduction into the human body. A heating device heats the gas in the introduction channel to substantially the temperature of the human body.

16 Claims, 2 Drawing Sheets

U.S. PATENT DOCUMENTS

| | | | |
|---|---|---|---|
| 5,411,474 A * | 5/1995 | Ott et al. | 604/26 |
| 5,423,741 A * | 6/1995 | Frank | 604/26 |
| 5,431,676 A * | 7/1995 | Dubrul et al. | 606/185 |
| 5,549,565 A * | 8/1996 | Ryan et al. | 604/167.03 |

* cited by examiner

INSTRUMENT THAT CAN BE INSERTED INTO THE HUMAN BODY

RELATED APPLICATIONS

This patent application is a divisional of U.S. patent application Ser. No. 08/946,799, filed Oct. 8, 1997, now issued as U.S. Pat. No. 6,814,714, which is a continuation of U.S. patent application Ser. No. 08/530,150, filed Sep. 29, 1995, now abandoned, which is the national stage entry of International Patent Application No. PCT/DE94/00663, filed Jun. 15, 1994, which claims priority to German Patent Application No. DE 43 19 630.6-35, filed Jun. 15, 1993.

FIELD OF THE INVENTION

The present invention relates to an instrument that can be inserted into the human body, this instrument being provided with at least one channel for fluid and, in particular a gas, which is introduced into the inside of the body.

BACKGROUND OF THE INVENTION

By way of illustration in laparoscopic operations, it is usually necessary to introduce a fluid and, in particular a gas, such as by way of illustration $CO_2$ into the body cavity into which incision was made in order that the cavity does not collapse due to the "external pressure".

With increasing duration of the operation, the number of incisions as well as the frequency of changing the instruments requires not only large amounts of insufflation gas, but also high insufflation rates. This is especially the case in HF surgery and laser treatment in which the gas has to remove additionally occurring smoke, etc. In the past, flow rates of a few liters per minute used to suffice, however, for some time increasingly higher flow rates are demanded.

However, even at flow rates in the 5 to 7 l/min range, the patient suffers hyperthermia, i.e. a local drop in temperature distinctly below the body temperature. If (insufflation) devices having even higher outputs, which in the case of the devices that are available on the market reaches up to 15 l/min, or even insufflation devices having flow-through rates up to 40 l/min are employed, as described in the patent literature, the problem of hyperthermia is even more serious than with conventional devices.

Therefore, it has been suggested to provide a means of heating the fluid in the insufflation device. In particular, with gas insufflation devices there is the problem of heating the gas in the insufflation device, because the gas has little thermal capacity, it cools off again in the supply tube on the way to the patient.

Thus, whenever the gas is heated only in the insufflation device, it is necessary to heat the gas to a higher temperature than is actually desired in order that the gas enters the human body "just" at a temperature that corresponds to the body temperature (37° C.). However, this has the drawback that the inertia of the system due to the long tube usually required is large if deviations of the temperature from the desired temperature, i.e. the control constant, is large and therefore the temperature constancy is small due to normal fluctuations. The gas therefore may even be introduced at a too high temperature inside the body.

In another attempt to solve the problem of the patient's hyperthermia, notably a device sold by Wisap, Sauerlach under the name "Flow-Therme" uses an additional heatable tube that connects the actual insufflation device to the instrument to be inserted into the human body.

This solution attempt, too, does not ensure optimum temperature control, because the control constant is large due the length of the tube and the possibly strongly varying surrounding conditions along the tube. Moreover, a heatable tube is less pliant and heavier due to the integrated heating means than a normal tube. Thus, it is not as easy to handle as a normal tube.

SUMMARY OF THE INVENTION

The object of the present invention is to ensure in introduction of at least one fluid and, in particular at least of a gas, into the body, excellent temperature control and, in particular, constancy of temperature of the fluid introduced into the body and, in particular, of the introduced gas.

An element of the present invention is that the instrument is provided with a heating means for the fluid. The heating means can heat the fluid and, in particular the gas, alone or in addition to a heating means in the insufflation device as well as, if need be, to a "supporting" heating means in the insufflation tube. Preferred at any rate is if the heating means of the instrument "assumes" "control" of the control procedure.

Disposal of the heating device in the, or immediately before the, human body, notably in or near the instrument utilized in the human body, ensures that optimum temperature control with short control constants can occur in such a manner that the fluid, that is the rinsing fluid or preferably the gas, having excellent constancy of temperature is introduced into the body cavity.

Another advantage of the invented instrument is that the instrument is heated by the heating means itself as well as by the heated fluid. This prevents the instrument and, in particular, an endoscope optics disposed therein, from fogging up. It is especially advantageous if the heating means surrounds that part of the instrument that accommodates the optical system of the system and, in particular of an endoscope, because this ensures optimum heating not only of the fluid but also of the "sensitive" parts of the instrument.

Furthermore, a conventional supply tube of any length, in particular, a length that can be varied from application to application can be utilized between the insufflation device and the instrument.

According to certain embodiments, the heating means can be integrated into the instrument itself. This design has not only the advantage that the optics located in the instrument are, if need be, heated directly along with the instrument, but also, which is not apparent at first glance, that it improves the balance of the weight of the instrument.

Although one usually tries to design the instruments as lightly as possible, this principle is not adhered to with laparoscopes utilized in conjunction with a $CO_2$ laser. In order to compensate for the weight of the $CO_2$ laser or the arm connected to this laser, the instrument has to be designed heavier than usual. This requirement can be easily met by building the heating means into the instrument.

As an alternative, the heating means can be disposed in a separate housing which is provided with a fluid inlet and a fluid outlet which is connected via a short piece of tube to the proximal fluid inlet of the instrument itself. This design not only prevents undesirable top-heaviness in specific applications, but also permits easy upgrading of already existing instruments in such a manner that they functionally comply with the instrument proposed by the present invention.

The use of an electric heating coil and its special design in accordance with certain embodiments is now described.

In the aforementioned alternative, in which the heating means is disposed outside the body, it is preferable if the heating means is provided in the part of the instrument which remains outside the human body. This permits accommodating the heating means as well as parts of the control unit in the thicker than usually designed proximal part of the instrument without impairing the functions of the instrument.

Another alternative which is suited particularly for existing instruments is now set forth. The heating means is provided in a separate housing which is connected in one piece to the conventionally designed instrument. This alternative permits upgrading existing instruments as well.

In certain embodiments, the heating means is provided with at least one temperature sensor whose output signal is applied to a control means which controls the power delivered to the heating means, thereby permitting not only control of the heating output but also control of the set temperature.

In another embodiment, there are provided at least two temperature sensors whose output signals are compared for checking the function of the temperature sensors, thereby permitting relatively precise detection of malfunctions.

It is advantageous if the temperature sensor or sensors are disposed as close as possible to the channel through which the fluid flows. Independent of the exact design of the temperature sensors, it is advantageous if a temperature sensor which can release a safety circuit is disposed as close as possible to the distal end of the instrument.

Many different evaluation algorithms can be used to control the invented instrument. These strategies can be stored in a program memory and called up upon demand. In any event, any instrument and, in particular, a trocar as well as an as such known laparoscope for surgical applications can be employed in conjunction with the present invention.

BRIEF DESCRIPTION OF THE DRAWINGS

The present invention is made more apparent in the following by way of example without the intention of limiting the scope or spirit of the overall inventive idea using preferred embodiments with reference to the drawings to which are explicitly referred for the disclosure of all invented details not explained more closely herein.

DETAILED DESCRIPTION OF AN EMBODIMENT OF THE INVENTION

Figure 1:
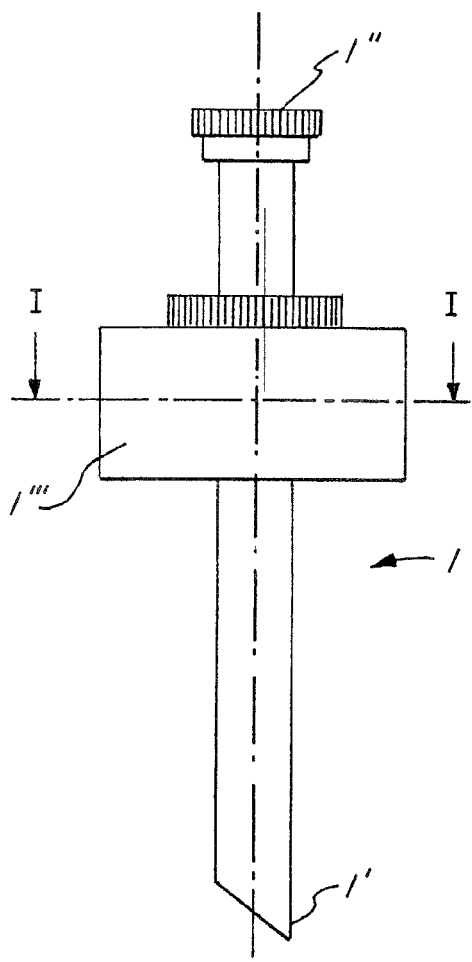
FIG. 1 shows a lateral view of a first preferred embodiment of an invented instrument.

FIG. 1 shows an instrument which can be inserted inside a human (or animal) body and which, without limiting the scope and spirit of the present invention is an as such known trocar 1 having a distal end 1' and a proximal end 1". The trocar has a cavity 2 extending in the longitudinal direction. Into this cavity 2 (by way of illustration) not depicted endoscope optics can be inserted in such a manner that additionally a channel (having a ring-shaped cross section) is formed for a fluid and, in particular, a gas such as $CO_2$. Of course, another channel separated from the other insertable instruments may be provided for the to be introduced fluid.

For the introduction of a gas in the channel formed by inserting an instrument or an already existing channel, a connection 3 is provided, which by way of illustration can be a conventional luer-lock connection or a tube nozzle, which connection 3 is provided with a cock 4. In the case of large flow-through rates, a connection having a larger diameter than the one which is usually used in a trocar can also be employed.

For heating the cold gas or the gas already preheated by a heating means in an insufflation device 12, which is joined via a tube 13 to connection 3, a heating means 5 having a connection 5' is provided. This heating means has at least one electric heating coil 6, which surrounds the channel through which the fluid is conducted. In the shown preferred embodiment, the heating means 5 is provided in the "thicker" part of the trocar, which remains outside the human body.

Furthermore, the heating means 5 is provided with at least one temperature sensor 7, whose output signal is applied to a not depicted control or adjustment means which controls the electric power applied to the heating coil 6. Preferably, at least two temperature sensors are provided whose output signals are compared for checking the function of the temperature sensors. The temperature sensor or sensors should be disposed as close as possible to the channel through which the fluid flows. Thus the control constants are small even in the case of high flow rates up to 40 l/min and more as well as of greatly varying flow rates.

In the following figures, the same reference numbers stand for the same respectively similar parts, obviating renewed introduction.

Figure 2:
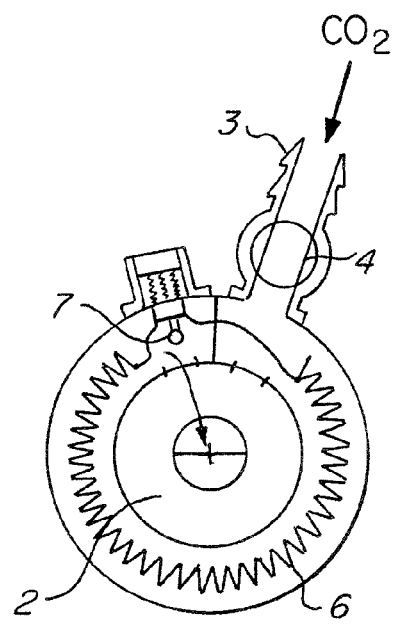
FIG. 2 shows a section at I-I in FIG. 1.
Figure 3:
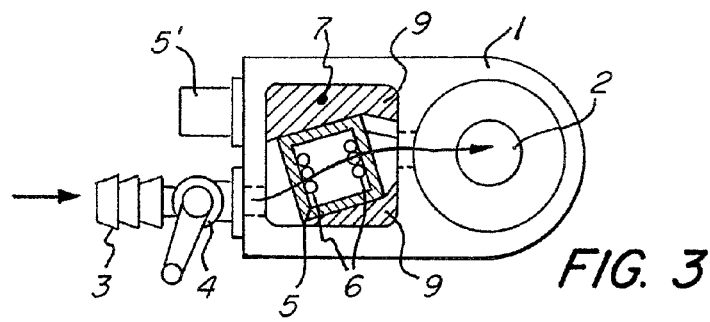
FIG. 3 shows a variant of the preferred embodiment depicted in FIG. 1.

FIG. 3 shows a partial section of a top view of a modification of the preferred embodiment depicted in FIGS. 1 and 2. In this preferred embodiment, the heating means is accommodated in a lateral addition. The heating coil 6 is designed cube-shaped and disposed in the channel which joins the connection 3 including cock 4 to the cavity 2 in the instrument and 9 stands for a casting compound.

Figure 4:
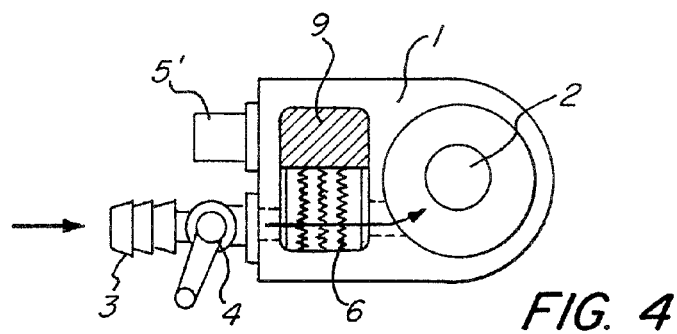
FIG. 4 shows another variant of the preferred embodiment depicted in FIG. 1.

FIG. 4 also shows a partial section of a top view of a further modification of the preferred embodiment depicted in FIGS. 1 and 2. In this modification, the heating coil is designed as a flat, electric heated element.

Figure 5:
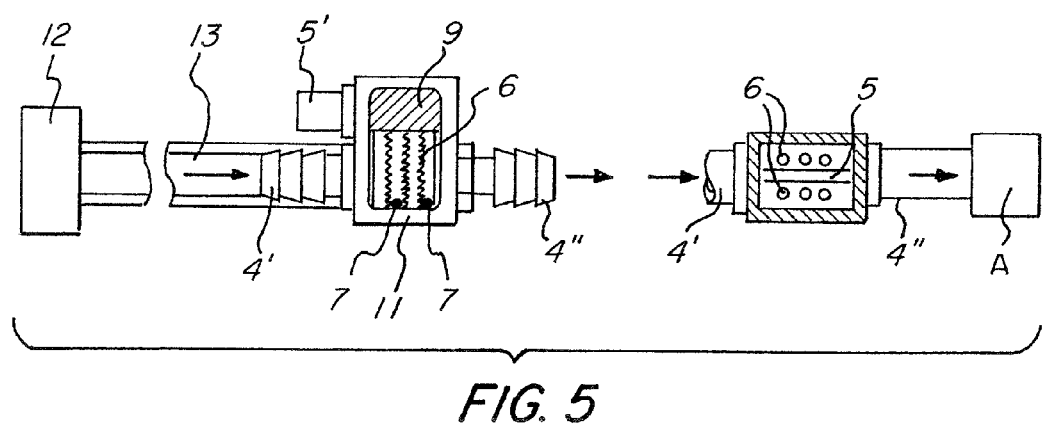
FIG. 5 shows a second preferred embodiment of the present invention.

FIG. 5 shows a partial section of a top view and a lateral view of a second preferred embodiment of the present invention. In this preferred embodiment, the heating means is not accommodated in the first instrument A itself, but rather in an addition which is provided with a housing 11 which is provided with a tube nozzle 4' which functions as an inlet and a tube nozzle 4" which functions as an outlet. The addition is connected to the inlet 3 of the instrument A not depicted in FIG. 5 by means of the tube nozzle 4" and a short tube. Located in the housing 11 is a fluid channel in which the heating coil designed as a flat element is disposed and 5' stands for the connection for the heating means.

In the preceding the present invention has been described using a preferred embodiment without the intention of limiting the scope and spirit of the overall invention. By way of illustration, a heating means operating with a heat exchanger can be employed instead of an electric heating means.

Of course, the design of the heating coils is not restricted to the preferred embodiments described in the preceding, but rather many different radiators can be employed which, by way of illustration can be designed as a "tubular heating element".

The instrument which in accordance with the present invention is equipped with a heating means is also not restricted to the explicitly mentioned trocars and laparoscopes described in the preceding.

What is claimed is:

1. An endoscopic instrument comprising:
a first endoscopic instrument part adapted for introduction into a cavity of a human body and having an introduction channel therein for passage of gas therethrough;
an insufflation device;
a second instrument part having a connection channel therein adapted to be connected to said first instrument part introduction channel;
a tube disposed between said second instrument part and said insufflation device, said tube spatially separating said second instrument part from said insufflation device, but connecting said second instrument part and said insufflation device to provide gas, at a flow rate suitable for insufflation of a human body cavity, from said insufflation device through said tube and said connection channel to said introduction channel for introduction into the human body;
a heating device for heating the gas in said introduction channel to substantially the temperature of the human body, wherein said heating device is provided in said second instrument part; and
wherein said endoscopic instrument comprises a trocar for performing an endoscopic procedure to the human body.

2. The endoscopic instrument as claimed in claim 1, wherein said heating device comprises an electrical heating coil.

3. The endoscopic instrument as claimed in claim 2, wherein said heating coil is flat.

4. The endoscopic instrument as claimed in claim 1, further comprising a housing connected to said endoscopic instrument and having said heating device therein.

5. The endoscopic instrument as claimed in claim 1, further comprising a temperature sensor for supplying a signal indicative of the gas temperature.

6. The endoscopic instrument as claimed in claim 5, wherein said temperature sensor is positioned adjacent said connection channel to provide the signal to a regulator for said heating device.

7. The endoscopic instrument as claimed in claim 5, wherein said temperature sensor is positioned adjacent the distal end of said introduction channel to provide the signal to a safety shut-off for said heating device.

8. The endoscopic instrument as claimed in claim 1, further comprising two temperature sensors, each temperature sensor supplying a signal indicative of the gas temperature; and means for comparing the signals from the two temperature sensors to provide a signal to a regulator for said heating device.

9. An endoscopic instrument comprising:
a first endoscopic instrument part adapted for introduction into a cavity of a human body and having an introduction channel therein for passage of gas therethrough;
an insufflation device;
a second instrument part comprising a housing having a gas inlet and a gas outlet and having a connection channel therein between the gas inlet and the gas outlet, the gas outlet adapted to be connected to said first instrument part introduction channel, and the gas inlet adapted to be connected to said insufflation device;
via a tube disposed between said second instrument part and said insufflation device, said tube spatially separating said second instrument part from said insufflation device, but connecting said second instrument part and said insufflation device to provide gas, at a flow rate suitable for insufflation of a human body cavity, from said insufflation device through said connection channel to said introduction channel for introduction into the human body;
a heating device formed integrally within the housing of said second instrument part, said heating device for heating the gas in said introduction channel to substantially the temperature of the human body; and
wherein said endoscopic instrument comprises a trocar for performing an endoscopic procedure to the human body.

10. The endoscopic instrument as claimed in claim 9, wherein said heating device comprises an electrical heating coil.

11. The endoscopic instrument as claimed in claim 10, wherein said heating coil is flat.

12. The endoscopic instrument as claimed in claim 9, wherein said heating device is provided in said second instrument part.

13. The endoscopic instrument as claimed in claim 9, further comprising a temperature sensor for supplying a signal indicative of the gas temperature.

14. The endoscopic instrument as claimed in claim 13, wherein said temperature sensor is positioned adjacent said connection channel to provide the signal to a regulator for said heating device.

15. The endoscopic instrument as claimed in claim 13, wherein said temperature sensor is positioned adjacent the distal end of said introduction channel to provide the signal to a safety shut-off for said heating device.

16. The endoscopic instrument as claimed in claim 9, further comprising two temperature sensors, each temperature sensor supplying a signal indicative of the gas temperature; and means for comparing the signals from the two temperature sensors to provide a signal to a regulator for said heating device.

* * * * *